US00PP25871P2

(12) United States Plant Patent
Tully

(10) Patent No.: US PP25,871 P2
(45) Date of Patent: Sep. 8, 2015

(54) ***HEBE* PLANT NAMED 'TULL 302'**

(50) Latin Name: ***Hebe* hybrid**
Varietal Denomination: Tull 302

(71) Applicant: Padraig Tully, Richardstown (IE)

(72) Inventor: Padraig Tully, Richardstown (IE)

(73) Assignee: TULLY NURSERIES, LTD., Richardstown (IE)

( * ) Notice: Subject to any disclaimer, the term of this patent is extended or adjusted under 35 U.S.C. 154(b) by 135 days.

(21) Appl. No.: 13/986,859

(22) Filed: Jun. 12, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

UPOV: Plant Variety Database—International Union for the Protection of New Varieties of Plants, Jan. 15, 2015, culitvar name 'Tull 302' (1 page total).*

* cited by examiner

*Primary Examiner* — Susan McCormick Ewoldt
(74) *Attorney, Agent, or Firm* — Penny J. Aguirre

(57) ABSTRACT

A new cultivar of *Hebe*, 'Tull 302', characterized by its compact and slightly spreading plant habit, its variegated foliage with green centers and creamy white margins, its greyed-purple young shoots, and its ability to consistently produce healthy plants.

2 Drawing Sheets

Botanical classification: *Hebe* hybrid.
Cultivar designation: 'Tull 302'.

BACKGROUND OF THE INVENTION

The present invention relates to a new and distinct cultivar of *Hebe*, botanically of hybrid origin and known as *Hebe* 'Tull 302' and will be referred to hereafter by its cultivar name, 'Tull 302'. 'Tull 302' is grown for use as a container plant and as a landscape shrub.

The new cultivar was discovered as a naturally occurring branch mutation of 'Hedgehog' (not patented) in a trial garden in the Inventor's nursery in July of 2008 in Ballyboughal, Dublin County, Ireland.

Asexual propagation of the new cultivar was first accomplished by the Inventor by softwood cuttings in Ballyboughal, Dublin County, Ireland in July of 2008. Asexual propagation by softwood stem cuttings has been determined that the characteristics of the new cultivar are stable and are reproduced true to type in successive generations.

SUMMARY OF THE INVENTION

The following traits have been repeatedly observed and represent the characteristics of the new cultivar, which in combination distinguish 'Tull 302' as a new and distinct cultivar of *Hebe*.

1. 'Tull 302' exhibits a compact and slightly spreading plant habit.
2. 'Tull 302' exhibits foliage with green centers and creamy white margins.
3. 'Tull 302' exhibits greyed-purple young shoots.
4. 'Tull 302' consistently produces healthy plants.

The parent plant of 'Tull 302', 'Hedgehog', differs from 'Tull 302' in having non-variegated dark green foliage and in having smaller leaves. 'Tull 302' can be most closely compared to the cultivars 'Heartbreaker' (not patented) and 'Frozen Flame' (U.S. Plant Pat. No. 20,376). 'Heartbreaker' differs from 'Tull 302' in having longer and narrower leaves that are variegated with grey-green centers and creamy white margins. 'Frozen Flame' differs from 'Tull 302' in having narrower and slightly shorter leaves that are variegated with green and red centers and dark pink margins.

BRIEF DESCRIPTION OF THE DRAWINGS

The accompanying colored photographs illustrate the overall appearance and distinct characteristics of the new *Hebe*. The photographs were taken of a plant approximately three years in age grown outdoors in a 25-cm container in Boskoop, The Netherlands.

The photograph in FIG. 1 is a side view of 'Tull 302'.

Figure 1:
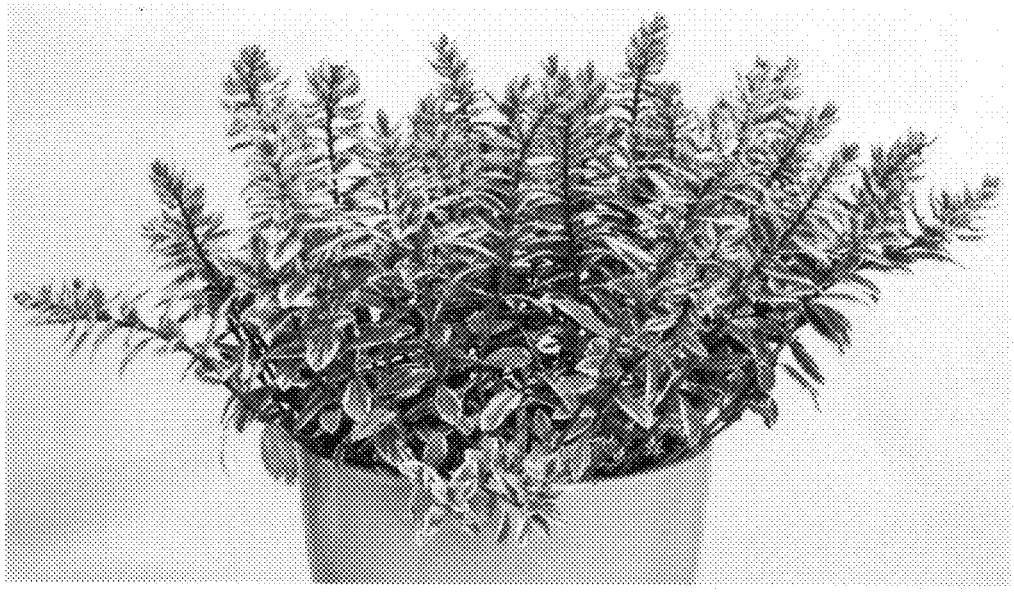
Figure 2:
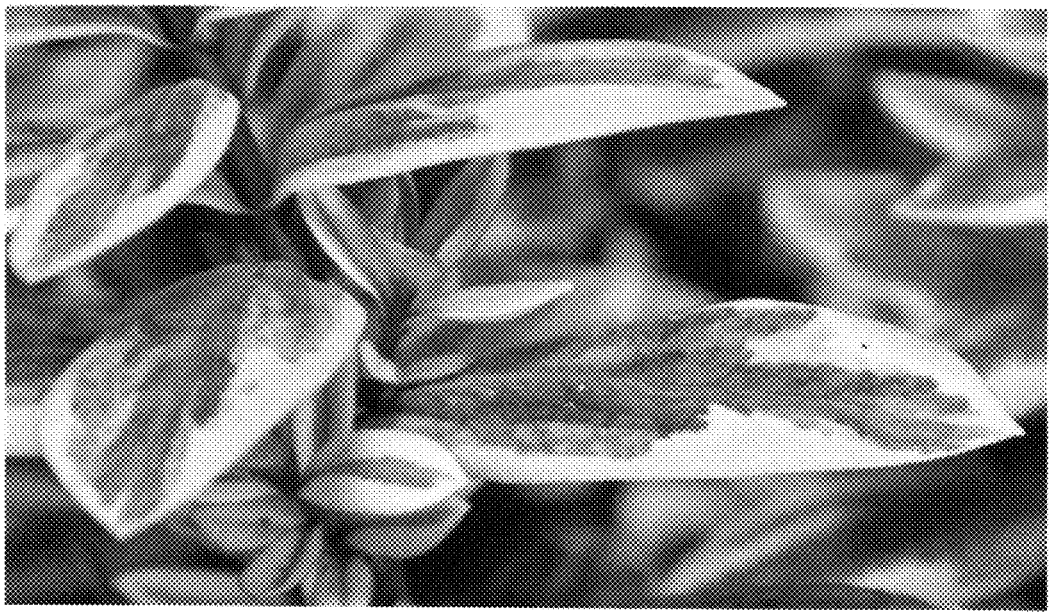

The photograph in FIG. 2 provides a close-up view of the foliage of 'Tull 302'.

Figure 3:
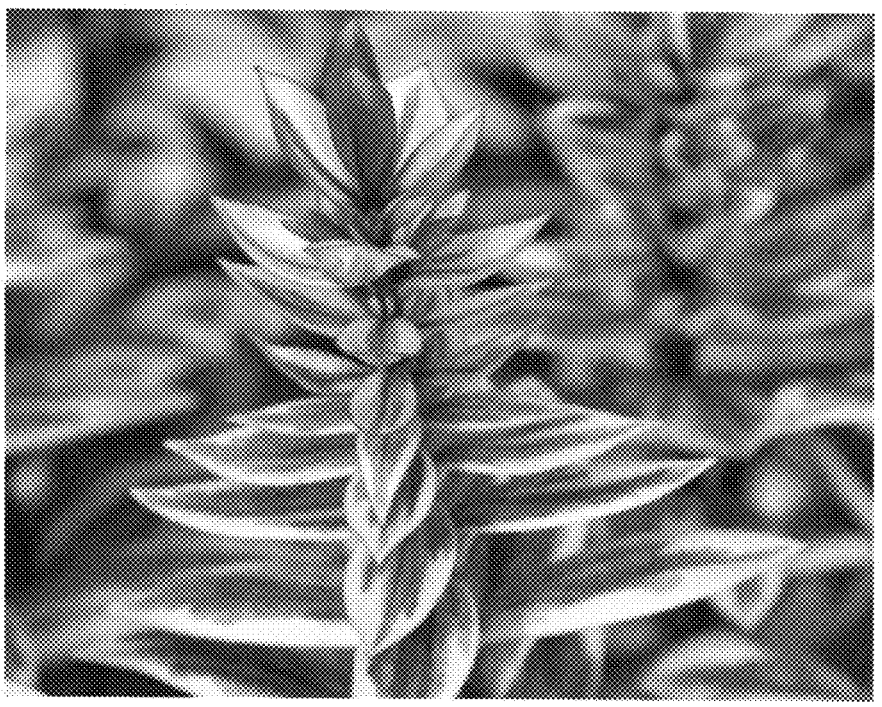

The photograph in FIG. 3 provides a close-up view of the new shoots of 'Tull 302'.

The colors in the photographs may differ slightly from the color values cited in the detailed botanical description, which accurately describe the colors of the new *Hebe*.

DETAILED BOTANICAL DESCRIPTION OF THE PLANT

The following is a detailed description of three year-old plants of the new cultivar as grown outdoors in 25-cm containers in October in Boskoop, The Netherlands. Plants were grown under average day temperatures of 10° to 23° C. and average night temperatures of 1° to 14° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General plant characteristics:

*Plant type.*—Evergreen shrub.

*Plant habit.*—Compact and slightly spreading.

*Height and spread.*—Reaches about 29 cm in height and 56 cm in width.

*Environmental stresses.*—Highly tolerant to rain and wind.

*Hardiness.*—At least in U.S.D.A. Zone 8.

*Diseases.*—Not more susceptible to pests and diseases than other *Hebe* varieties.

*Root description.*—Dense, fibrous to slightly fleshy.

*Root development.*—An average of 28 days for root initiation with a rooted cutting produced after an average of 120 days.

*Growth rate.*—Moderate.

*Propagation.*—Softwood cuttings.

Stem description:

*Stem size.*—Lateral branches are an average of 25.8 cm in length and 4 mm in diameter.

*Stem shape.*—Rounded.

*Stem color.*—Young and older stems N186C in color.

*Stem surface.*—Slightly glossy, glabrous, and smooth in texture.

*Stem strength.*—Strong.

*Internode length.*—Average of 1.2 mm.

*Branching habit.*—Moderate to high, average of 56 lateral branches, 25.8 cm in length and 4 mm in diameter.

Foliage description:

*Leaf shape.*—Elliptic.

*Leaf division.*—Single.

*Leaf base.*—Cuneate.

*Leaf apex.*—Acute.

*Leaf venation.*—Pinnate, upper surface in the margin a blend of 11B and 160B in color and in the center a blend of N137A to 147A in color, lower surface 147B in color.

*Leaf margins.*—Entire.

*Leaf attachment.*—Sessile.

*Leaf arrangement.*—Opposite, decussate.

*Leaf surface.*—Smooth, upper surface slight glossy, lower surface very slightly glossy.

*Leaf color.*—Young upper surface; 147A in color with broad margins colored 185D, young lower surface; 187A in color with broad margins colored 186D, mature upper surface; margins broad and irregular 11B and 160B in color and centers are a blend of N137A and 147A marbled with 191C, mature lower surface; margins broad and irregular 11B and 160B in color and centers are a blend of 147B and 191A.

*Leaf number.*—Average of 44 per lateral branch.

*Leaf size.*—5.2 cm in length and 2.2 cm in width.

*Leaf aspect.*—Held nearly horizontal to slightly upright to stem.

*Leaf fragrance.*—None.

Flower description: No flowers observed to date.

It is claimed:

1. A new and distinct cultivar of *Hebe* plant named 'Tull 302' as herein illustrated and described.

* * * * *